(12) United States Patent
Zahler et al.

(10) Patent No.: US 6,236,881 B1
(45) Date of Patent: May 22, 2001

(54) METHOD AND APPARATUS FOR DIFFERENTIATING AND PROCESSING IMAGES OF NORMAL BENIGN AND PRE-CANCEROUS AND CANCEROUS LESIONED TISSUES USING MIXED REFLECTED AND AUTOFLUORESCED LIGHT

(75) Inventors: Mordechay Yacov Zahler, Modiin; Nitzan Sneh, Ramat Hasharon, both of (IL)

(73) Assignee: Contec Medical Ltd., Ramat Hasharon (IL)

( * ) Notice: Subject to any disclaimer, the term of this patent is extended or adjusted under 35 U.S.C. 154(b) by 0 days.

(21) Appl. No.: 09/299,248

(22) Filed: Apr. 26, 1999

(51) Int. Cl.[7] .................................................. A61B 5/05
(52) U.S. Cl. ............................................................ 600/476
(58) Field of Search ............................................ 600/476

(56) References Cited

U.S. PATENT DOCUMENTS 5,749,830 * 5/1998 Kaneko et al. ....................... 600/476

OTHER PUBLICATIONS

S. Montan, K. Svanberg, and S. Svanberg; Multicolor imaging and contrast enhancement in cancer–tumor localization using laser–induced fluorescence in hematoporphyrin–derivative–bearing tissue; Feb. 1985; Optics Letter/vol. 10, No.2 pp. 56–58.

Robert R. Alfano et al.; Laser Induced Fluorescence Spectroscopy from Native Cancerous and Normal Tissue*; IEEE Journal of Quantum Electronics, vol. QE–20, No. 12, Dec. 1984; pp 1507–1511.

R. R. Alfano et al.; Fluorescence Spectra from Cancerous and Normal Human Breast and Lung Tissues; IEEE Journal of Quantum Electronics, vol. QE–23, No. 10, Oct. 1987; pp. 1806–1811.

Dirk G. Soenksen et al.; Use of a novel spectral bio–imaging system as an imaging oximeter in intact rat brain;SPIE vol. 2679; pp. 182–189.

Richard M. Levenson and Daniel L. Farkas; Digital Spectral Imaging for Histopathology and Cytopathology; SPIE vol. 2983 pp. 123–135.

Prof. H. Vanden Bergh; Fluorescence Diagnosis of Genitourinary Cancer; Nov. 1997; pp. 1–6.

Carrie K. Brookner et al.; Cervical Fluorescence of Normal Women; Lasers in Surgery and Medicine 24:29–37(1999) Wiley–Liss, Inc.

* cited by examiner

Primary Examiner—William E. Kamm
(74) Attorney, Agent, or Firm—Helfgott & Karas, P.C.

(57) ABSTRACT

A computerized apparatus implementing a real time detection algorithm for non drug-activated imaging diseases, e.g. in cervical and bladder tissues. The apparatus employs an ultra-bright metal halide light source, utilizing its definite and sharp purple & green spectral lines, for producing excitation light to excite the tissue to generate a combined reflection & autofluorescence light from the tissue. An advanced optical system, coupled to a digital color & multi spectral camera, is used for collecting the combined reflection & autofluorescence light from the inspected tissues. This system contains a miniature filter wheel, running synchronously with the camera video frame—rate (i.e.—30 frames/sec for NTSC or 25 frames/sec for PAL). Utilizing this synchronously-running filter wheel and an advanced frame grabber for real time buffering and multi tasked spectral and spatial segmentation algorithm implementations, the malignant and pre-malignant tissues are automatically detected and differed from regular/benign tissues. Moreover, these (dysplasm/neoplasm) cancerous and/or pre-cancerous lesions are marked in real time (as glow overlays) on a regular color image.

23 Claims, 7 Drawing Sheets

METHOD AND APPARATUS FOR DIFFERENTIATING AND PROCESSING IMAGES OF NORMAL BENIGN AND PRE-CANCEROUS AND CANCEROUS LESIONED TISSUES USING MIXED REFLECTED AND AUTOFLUORESCED LIGHT

BACKGROUND OF THE INVENTION

1. Field of Invention

The present invention relates generally to the field of spectral imaging. More specifically, the present invention is related to a method and apparatus for real time recognition and displaying of diseased tissue such as cancerous and pre-cancerous lesions. A physical model of the present invention is included herein in Appendix A and is hereby incorporated by reference.

The following definitions may assist in the understanding of terminology used throughout the specification:

photopic—relating to or being vision in bright light with light-adapted eyes that are mediated by the cones of the retina;

luminescence—low temperature emission of light (as by a chemical or physiological process); also, light produced by luminescence;

fluorescence—luminescence that is caused by the absorption of radiation at one wavelength followed by nearly immediate reradiation usually at a different wavelength and that ceases almost immediately when the incident radiation stops;

phosphorescence—luminescence that is caused by the absorption of radiation at one wavelength followed by delayed reradiation at a different wavelength and that continues for a noticeable time after the incident radiation stops;

Halogens—fluorine, chlorine, bromine, iodine and astatine. Each member has a valence of −1 and combines with metals to form halides, as well as metals and nonmetals to form complex ions.

halide—a binary compound of a halogen with a more electropositive element or radical metal halide;

dysplasia—abnormal growth or development (as of organs or cells);

neoplasia—the formation of tumors;

endoscope—an instrument for visualizing the interior of the body;

2. Discussion of Prior Art

Techniques for early screening, detection and diagnosis of pre-cancerous and cancerous tissues have been primarily limited to removal and testing of suspect tissue samples. Samples are typically tested in remotely located laboratory facilities using various known chemical and imaging techniques. Prior art methods lack accuracy and further fail to provide for real time screening and analysis.

One known prior art method of screening uses fluorescence emitted from the diseased tissues. Fluorescence has long been known as a tool used to detect cancerous tissue. Typically a tissue sample is removed from the body, injected with a spectrally responsive medium which in turn is selectively absorbed by the cancerous sections of the tissue sample. Once absorbed, a light source is used to illuminate the spectrally responsive medium and with cameras detect fluorescence. Other methods, without an injected liquid, use a laser of a shorter wavelength than fluorescence produced to excite the tissue. Sophisticated cameras are then used to detect the fluorescence. Examples of known prior art describing such methods are: U.S. Pat. Nos. 4,741,043; 4,965,725; 5,008,185; 5,093,866; 5,741,648; 5,507,287; 5,769,792 and 5,733,721 and articles "Multicolor Imaging and Contrast Enhancement in Cancer-tumor Localization Using Laser-induced Fluorescence in Hematoporphyrin-derivative-bearing Tissue"; "Laser Induced Fluorescence Spectroscopy from Native Cancerous and Normal Tissue"; "Fluorescence Spectra from Cancerous and Normal Human Breast and Lung Tissues"; "Use of a Novel Spectral Bio-imaging System as an Imaging Oximeter in Intact Rat Brain"; "Digital Spectral Imaging for Histopathology and Cytopathology"; "Fluorescence Diagnosis of Genitourinary Cancer" and "Cervical Fluorescence of Normal Women". In the prior art, as exemplified by Sekiguchi, U.S. Pat. No. 4,821,117, "Endoscopic System for Producing Fluorescent as Visible Images", issued Apr. 11, 1989, there is disclosed an endoscopic system which simultaneously displays a visible radiation image and a fluorescent image of an internal organ an a same display unit to identify any lesioned tissues in an internal human or animal organ. Sekiguchi requires that fluorescent material be applied to the tissue, At this point, the tissue is alternately illuminated with visible radiation and excitation radiation (laser light). A camera is synchronized with the light or emission sources such that reflected visible light is electronically captured and stored in a first buffer while the fluorescent image is captured and stored in a second buffer. The fluorescent image in the second buffer is intensified to a predetermined level. Both images are then applied to one or more video read heads for concurrent display. It is noted that tissue when exposed to laser light at selected frequencies can fluoresce over a spectrum of wavelengths.

In Alfano, U.S. Pat. No. 5,042,494, "Method and Apparatus for Detecting Cancerous Tissue using Luminescence Excitation Spectra", issued Aug. 27, 1991, the disclosed method illuminates a target tissue with a laser or monochromatic light source varied over a predetermined range of frequencies. This causes the tissues to fluoresce. The returns are then sampled for intensity, luminescence, and excitation spectra and the wavelengths at which maximum values for these attributes occur are determined. Alfano next compares these values with their counterparts in either known benign or lesioned tissues to determine the carcinomatoid status of the target tissue.

In a similar vein, Palcic et al., U.S. Pat. No. 5,769,792, "Endoscopic Imaging System for Diseased Tissue", issued Jun. 23, 1998, illuminates a target tissue with laser light to induce fluorescence excitation and white light for color imaging. This arrangement is limited in that it relies also on the autofluorescence contrast between lesioned and benign tissues for detection. Additionally, Palcic requires a multiple camera and elaborate beam splitting optical system in order to obtain multiple images.

Two examples of cancers which are treatable by early and proper diagnosis are cervical and bladder cancer. Cervical cancer is the third most common type of cancer in women. Approximately 2% of all women will develop some form of cervical cancer. Paramount to survival is early detection and treatment In men 40–80 years of age, bladder cancer is the fourth most common type of cancer. More than 40,000 cases are detected annually in the US alone. As with cervical cancer, early detection is necessary for optimal treatment. Known techniques for early screening include pap smears and colposcopy (with and without acetic acid) for cervical cancer and optically guided biopsy and cytology for bladder cancer.

Prior art methods fail to provide for real time screening and analysis critical to early and effective diagnosis. They also suffer from many drawbacks which make them impractical for use in the field such as the removal of a tissue sample from the body, eliminating any analysis in situ (at the place under inspection). Delays associated with typical laboratory analysis make it impossible to analyze the tissue in real time and create the possibility of laboratory errors such as contamination, lost or mixed-up results or a poorly trained staff's improper diagnosis. In addition, samples removed from the body are imaged at a microscopic level, typically a few microns, and therefore a determination of the extent, i.e. perimeter, of diseased tissue is not well represented Early malignant and pre-malignant and dysplastic lesions are often barely visible or even invisible under regular white-light video-scopes and are often missed by such prior art techniques. And finally, spectral analysis is limited to spatial analysis (pattern recognition) of the fluorescence.

Whatever the precise merits, features and advantages of the above cited references, none of them achieve or fulfills the purposes of the present invention. Accordingly, it is an object of the present invention to provide for a method and apparatus for real time recognition of diseased tissue.

It is another object of the present invention to provide for automatic detection of malignant and pre-malignant tissue by illumination of a target tissue with a light source whose characteristics concurrently enhance contrast between lesioned and benign tissue and facilitate removal of noise and other artifacts from resulting detected images without elaborate optical processing.

It is another object of the present invention to provide for a sharp image contrast between normal and malignant and pre-malignant tissues.

It is another object of the present invention to provide for a real time color image display of detected malignant and pre-malignant tissue on a regular video-scope.

It is another object of the present invention to provide for a method of "in situ" analysis of diseased tissue.

It is an additional object of the present invention to provide for "in vivo" recognition of diseased tissue.

It is an additional object of the present invention to include an analysis of diseased tissue using combined reflectance and autofluorescence.

It is an additional object of the present invention to combine multi-spectral and spatial (blob) segmentation and analysis.

It is an additional object of the present invention to be non-destructive of the target tissue and rely upon a macroscopic assessment rather than a microscopic evaluation of tissue samples or the like.

It is an additional object of the present invention to provide for a compact single camera architecture.

It is an additional object of the present invention to provide for a compact Metal Halide light source with special spectral characteristics with no need for special optical elements such as beam splitters, shutters, etc.

It is an additional object of the present invention to provide for a compact single camera architecture utilized for both color and diagnosing imaging.

It is an additional object of the present invention to provide for a system which enables visual detection discernable by technicians without highly specialized training It is an additional object of the present invention to provide for multi-usage for all diagnostics and regular video-scope color imaging (e.g. colposcopy, cystoscopy and other endoscopic usages).

These and other objects are achieved by the detailed description that follows.

SUMMARY OF THE INVENTION

Figure 1:
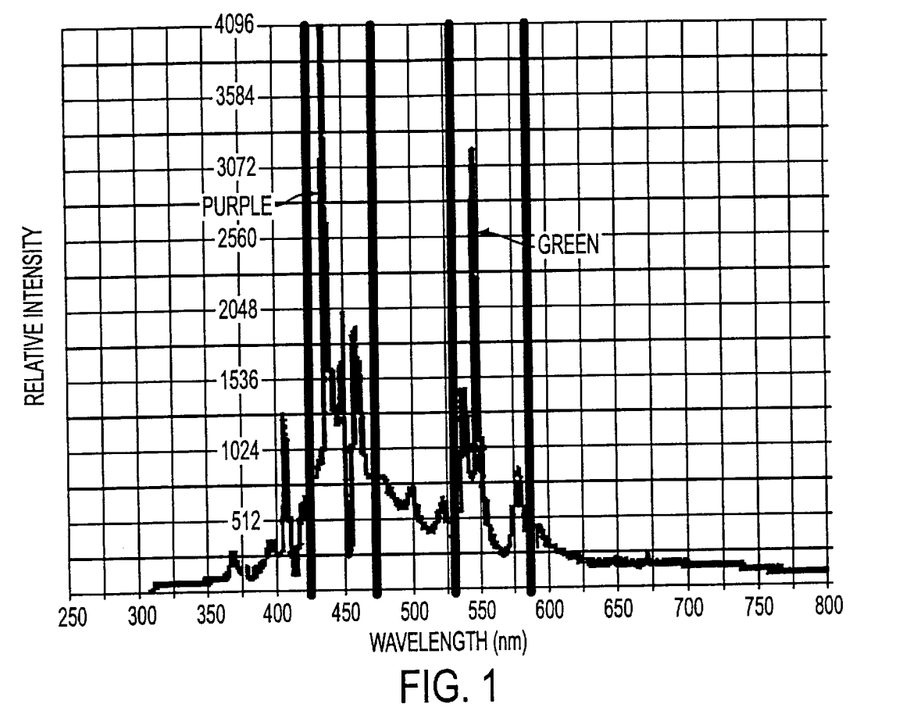
FIG. 1 illustrates a graph of the spectral density of a metal halide light source.

It was unexpectedly discovered that if a light were to illuminate target tissues and originate from an ultra-bright metal halide source, including double excitation bands in the purple 420–470 nm and green 520–580 nm wavelength regions (FIG. 1—spectral density of metal halide light source), then this spectrally mixed light would produce a combined reflectance and autofluorescence light. This combined light has an intensity that is different for normal tissue than for lesioned tissue. It was further discovered that this difference occurred within a special detection bandwidth between 500 nm peak with 40 nm defining half bandwidth. It was still further discovered that this light source was well-suited for concurrent color imaging in an ultra-bright light with an effective temperature of 5900 degrees. These essential properties permit using the light source for both photo dynamic diagnostics and regular color imaging with greater effectiveness then the prior art sources using flat or moderate spectra as generated by halogen or xenon sources.

The foregoing objects are believed satisfied by a multi-mode diagnostic method and device implementing these observations. The method and device of the invention are used in several diagnostic modes. These modes include (1) tissue image inspection only, (2) tissue image inspection and tissue image differentiation, and (3) tissue image differentiation only. In this specification, the description will be focused on the second mode since it combines the elements of both the first and third modes.

The method of the invention broadly contemplates two steps, namely, generating combined reflected and autofluoresced light by illuminating target tissue with the spectrally mixed light and specialty processing the combined light. After illuminating the tissue and inducing autofluorescing from the blue to the green spectral regions, the next step is to iteratively (1) electronically capture any reflected and autofluoresced light returns from the target tissues with at least one raster scanned and filtered image of the returns selected as a function of the mode of use, (2) process the filtered returns to enhance the contrast among normal and lesioned tissues and to subtract preselected types of artifacts, and (3) form and communicate one or more images of the processed returns.

The electronic capture defines a capture cycle in which several wheel mounted optical filters, each with special properties, rotate past a light gathering camera aperture. The output from each filter, as it rotates past the camera aperture, is a counterpart image of combined reflected and fluoresced light altered according to the filter properties. Synchronous with the rotation, each filtered image is raster scanned, digitized, and written into addressable separate buffers as arrays of digital values. Concurrently, one of the raster scanned filtered images can be used to provide an ordinary light color image on one or more color video monitors.

The electronic processing of the images involves several operations which are performed reiteratively. The key notion is to process each of the filtered images and form one or more special purpose arrays and utilize the arrays to modify the counterpart image. In this regard, the invention employs a multi-sectional filter arrangement comprising a photopic (A), maximal contrast (B), minimal contrast (C), and dark filter (D). Parenthetically, the output from filter A constitutes the full color image, the output from B is a high contrast image, the output from filter C is a low contrast reference level subtractive image and the dark filter provides a synchronization or blanking interval. The reiterative electronic processing for each turn of the filter wheel includes:

1) lesion feature location on the color image A using a multi-spectral array S in a logical combination operation (A∪S);
2) forming a gray level array difference C—B between the maximal B and minimal C contrast filter image array outputs and updating the maximal contrast image array B=(C—B);
3) computing an accumulated histogram H(B) as an adaptive threshold function of the maximal contrast array B of the fractional number of picture elements (pixels) of grey level values encountered in a predetermined grey level range;
(4) updating the multi-spectral array S by (a) forming a Boolean coded array E over array B using the function $$E = \begin{cases} 0 & \leftarrow H < t \\ 255 & \leftarrow H > t; \end{cases}$$

and (b) ascertaining the presence of binary large objects (BLOB) using BLOB analysis Boolean function p as a function of E's membership in a BLOB and modifying S such that:

$$p(E) = \begin{cases} 0 & \leftarrow E \notin BLOB \\ 1 & \leftarrow E \in BLOB \end{cases} \quad \text{and} \quad S = \begin{cases} 0 & \leftarrow p(E) = 0 \\ 255 & \leftarrow p(E) = 1 \end{cases}$$

BLOB analysis of images and the like is a standard process known in the art.

DESCRIPTION OF THE PREFERRED EMBODIMENTS

While this invention is illustrated and described in a preferred embodiment, the device may be produced in many different configurations, forms and materials. There is depicted in the drawings, and will herein be described in detail, a preferred embodiment of the invention, with the understanding that the present disclosure is to be considered as a exemplification of the principles of the invention and the associated functional specifications of the materials for its construction and is not intended to limit the invention to the embodiment illustrated. Those skilled in the art will envision many other possible variations within the scope of the present invention.

Figure 2:
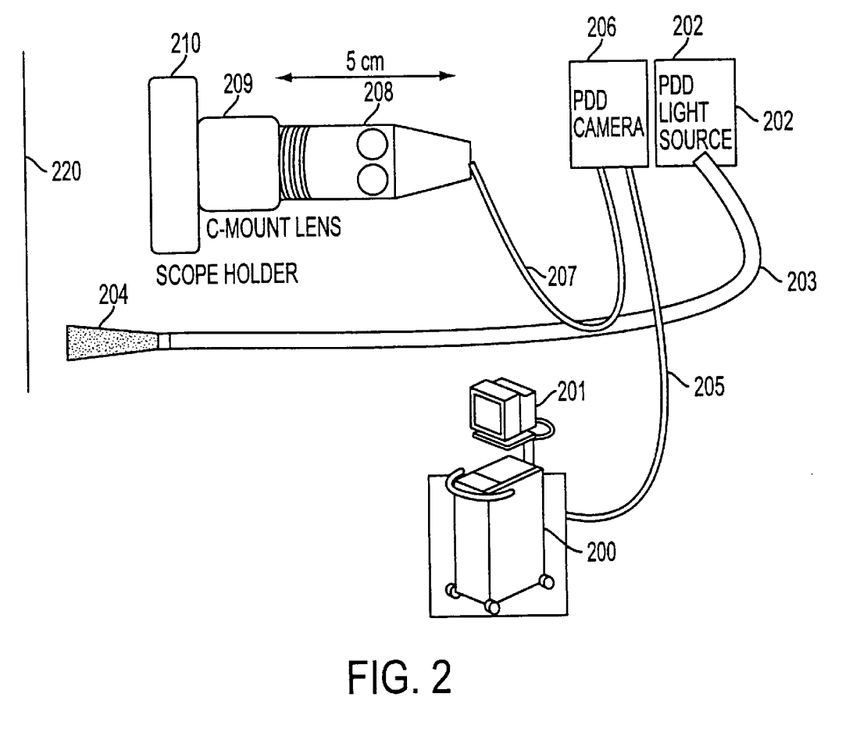
FIG. 2 illustrates a general overview of the photo dynamic diagnosis (PDD) system.

FIG. 2 illustrates an overview of a preferred embodiment of the present invention. The system is structured as a computerized medical imaging/processing system 200 implementing a real time detection algorithm for non drug-activated imaging of diseased tissues 220. The apparatus employs an ultra-bright metal halide light source 202 traveling through optical cable 203 to an output opening. The system utilizes the ultra-bright metal halide light source 202 because of its definite and sharp purple & green spectral lines (FIG. 1), for producing excitation light 204 to excite a target tissue 220 thereby generating a combined reflection & autofluorescence light from the tissue. The metal halide (HI) light source, in the preferred embodiment, is a Contec Medical 6050, generally available from Contec Medical LTD. Contec's ultra-compact 50 Watt metal halide light source provides the following specs and features: life time (>4000 hours); brightness illumination (color temperature) approx. 6000 K; cold source—no need for IR filter; ultra-compact size and weight (19×28×17 cm and 2.9 Kg) ; cooling system which keeps the cable connector completely cold and safe; highly and ultra-efficient illumination power (total output 3300 Lumens); can connect to multiple cable brands and definite spectral lines (FIG. 1) enabling various fluorescence diagnosis.

An advanced optical system 208/209 and scope holder 210 is coupled 207 to a digital color & multi spectral camera 206, used for collecting the combined reflection & autofluorescence light from the inspected tissues. Collected images are returned 205 to the computer 401 (FIG. 4) located within the computerized medical imaging/processing system 200 for processing and displayed on CRT 201 in real-time (approximately 0.2 seconds).

Figure 3:
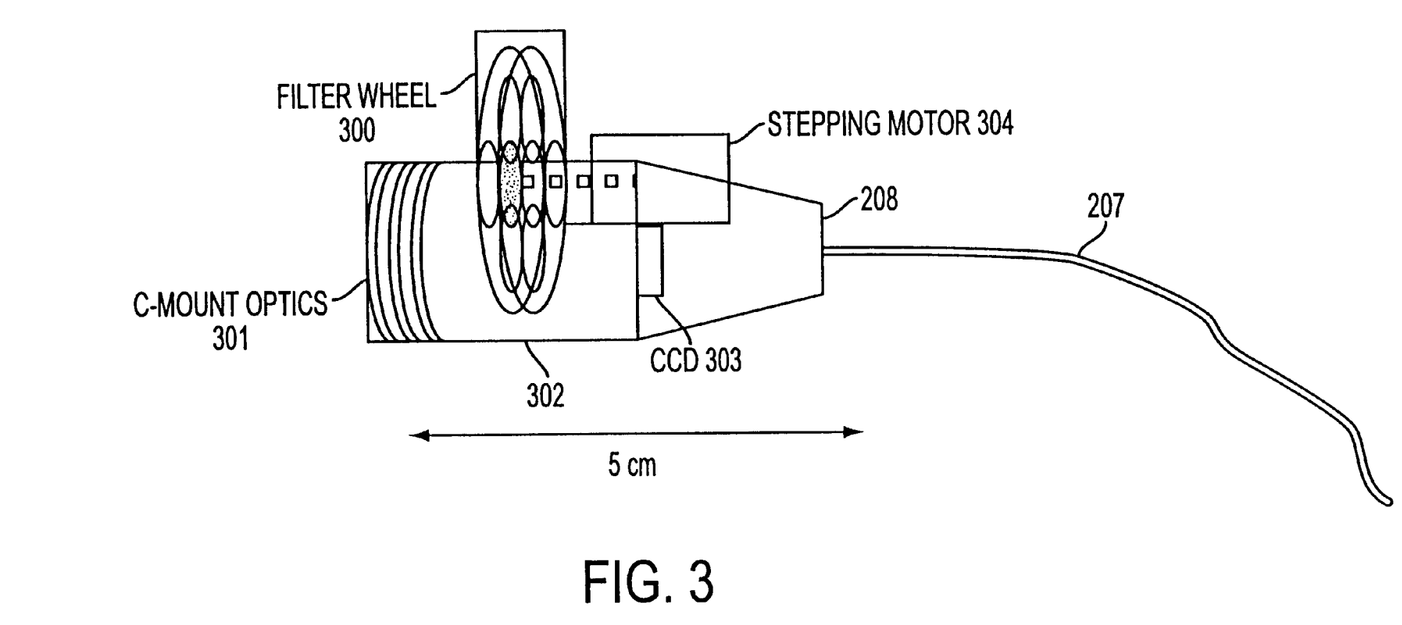
FIG. 3 illustrates the remote camera head with filter wheel and stepper motor.
Figure 4:
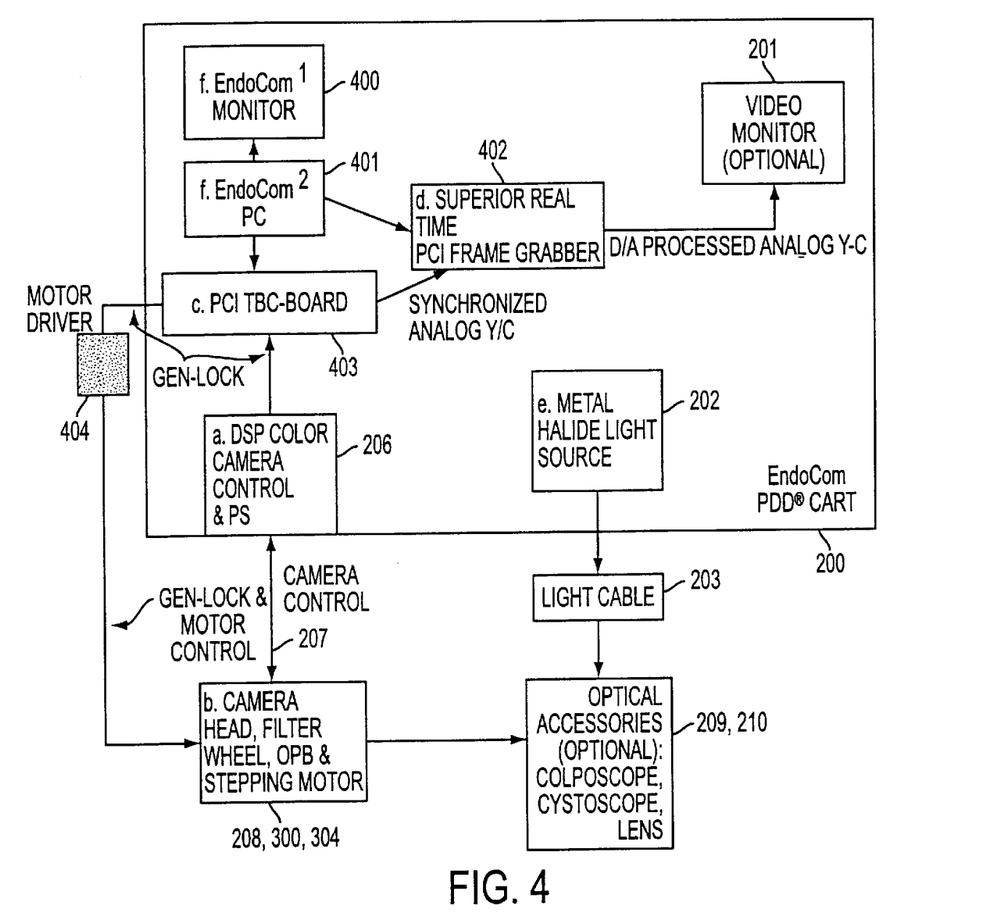
FIG. 4 illustrates a hardware overview of the entire system.

As shown in FIGS. 3 and 4, the advanced optical system includes a camera remote head 208, which further contains a miniature filter wheel 300 running synchronously with the camera video frame—rate (i.e.—30 frames/sec for NTSC or 25 frames/sec for PAL). The miniature filter wheel 300 is controlled (rotated) by a stepping motor 304 (e.g. Bayside). Synchronization of the filter wheel with the camera frame rate is performed via a time base corrector (TBC) 403 and the stepping motor driver interface 404. The TBC PC board 403 is located within the computer 401 which is part of the computerized medical imaging/processing system (EndoCom PDD®Cart) 200 and is standard off-the-shelf hardware used to optimally synchronize between the camera frame-rate, the frame grabber capture-timing and the stepper motor(filter wheel rotator) movement. High quality TBC is characterized by low jitter values (avoiding temporal synchronization mismatches). The preferred embodiment TBC board comprises: Gen-lock and Y/C inputs from the camera 206; Gen-lock (to stepping motor interface driver 404) and synchronized Y/C (to a frame grabber board 402) outputs. High end frame grabbers are available from companies such as IMAGING TECHNOLOGIES, DIPIX and MATROX, etc. Frame grabbers should have: advanced DSP processor for real time multi-tasked operations; expanded memory resources for image and LUT boarding; advanced and rich built-in signal processing libraries and LUT's for real time implementations; multiple inputs such as digital RGB, analog RGB, Y/C and composite.

A ½" or ¼" CCD chip 303 is selectively enabled at 752×528 (PAL) or 768×494 (NTSC) and is controlled by the camera 206 CPU. The main features of the DSP color camera 206 are: PAL/NTSC selectable, isp2000 proprietary VLSI digital video processor, DIP™—24 bit DSP ver 3.3 and $\frac{1}{50}$–$\frac{1}{30000}$ sec. fast—response automatic electronic shutter. The camera includes outputs: standard Y/C (s-video)

V=0.7 Vpp, Standard VBS V-1.0 Vpp 75 Ohm, Digital RGB(optional) and Sync out(Gen Lock output)—a train of rectangular shaped signals that synchronously imitates the image fields (odd and even) triggering. This is used in order to synchronize other cameras, or in the preferred embodiment, synchronous triggering of the stepping motor (i.e. rotating the filter wheel 300).

The filters within the filter wheel are:

1. Photopic (IR cut-off) filter for a regular, minimally distorted, color image
2. 500 nm peak/40 nm half-bandwidth filter - providing a maximal image-contrast between dysplastic/neoplasm, normal and benign superficial tissues. This filter acts to integrate the combined reflectance & autofluorescence image over a range of wavelengths in which the intensity for normal or benign tissue is substantially different from the intensity for diseased tissue.
3. 590 nm peak/20 nm half-bandwidth filter providing minimal image-contrast between dysplastic/neoplasm, normal and benign superficial tissues. This filter acts to integrate the combined reflectance & autofluorescence image over a range of wavelengths in which the intensity for normal or benign tissue is negligibly different from the intensity for diseased tissue.
4. optical photo bridge (OPB) dark filter used to indicate a starting point for synchronization purposes.

Utilizing this synchronously running filter wheel and an advanced frame grabber for real time buffering and multi tasked spectral and spatial segmentation algorithm implementations, the malignant and pre-malignant tissues are automatically detected and differed from normal/benign tissues. Moreover, these (dysplasm/neoplasm) cancerous and/or pre-cancerous lesions are marked in real time (as glow overlays) on a regular color image, enabling a simple 'plug & play' non-expert usage of the apparatus. This is displayed on a FIC-monitor 400 or alternatively—on a video monitor 201. Methods & algorithms include real time detection of malignant and pre-malignant lesions and seeding (spatial and spectral segmentation).

Software

The following is a computer program flow of the present invention for combined, real time, color & multi-spectral imaging of cancerous and pre-cancerous tissues, e.g. within a woman's cervix (through a gynecologist colposcope) or a man's bladder (through a urology cystoscope).

Figure 6A:
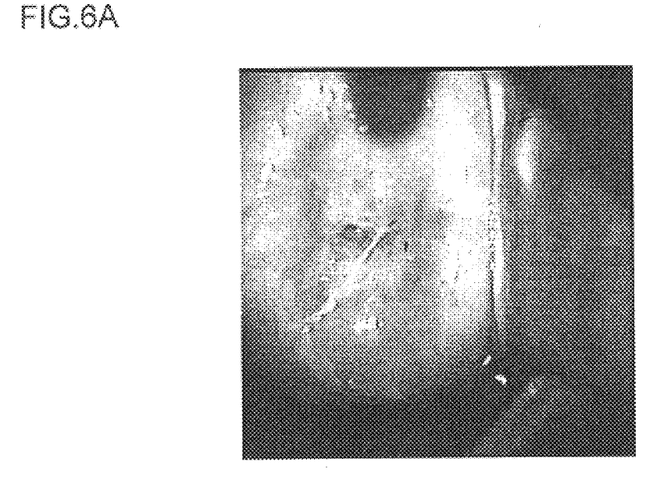
FIG. 6a illustrates a target tissue using a pure endoscopic mode using the present invention.
Figure 6B:
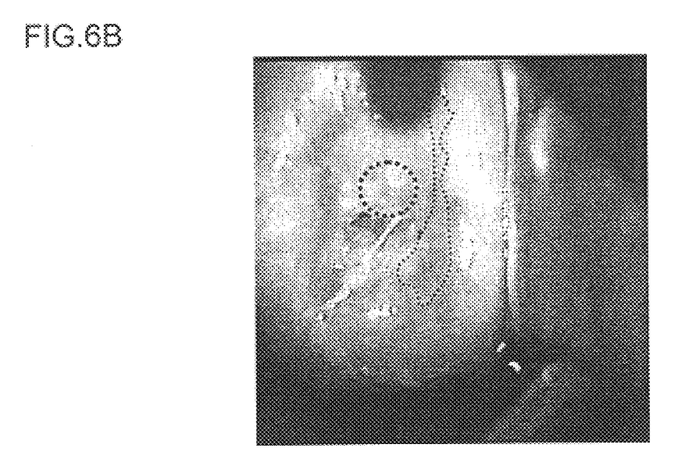
FIG. 6b illustrates a target tissue using a combined endoscopic and diagnostic mode using the present invention.
Figure 6C:
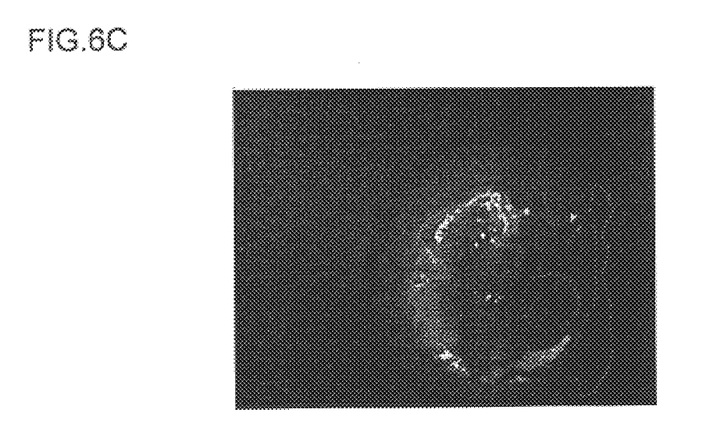
FIG. 6c illustrates a target tissue using a pure diagnostic mode using the present invention.

The apparatus can be operated in 3 modes as shown in FIGS. 6a–6c:

One—6a) Regular inspection (color) mode (filter-wheel locks on no. 1). No further algorithm is applied (in addition to the built-in camera DSP optimization).

Two—6b) Plug & Play-Combined color imaging (inspection) & automatic diagnostic detection (real time glow overlay of suspicious lesions 600 on a color image). Both multi-spectral & spatial segmentation methods are used, providing a negligible false-alarm appearance. (filter-wheel runs, adjusted to PAL/NTSC video rate)

Three—6c) Pure diagnostic mode (filter-wheel locks on no. 2). Only spatial segmentation algorithm is applied for detection of pre-malignancies and malignancies.

Figure 5:
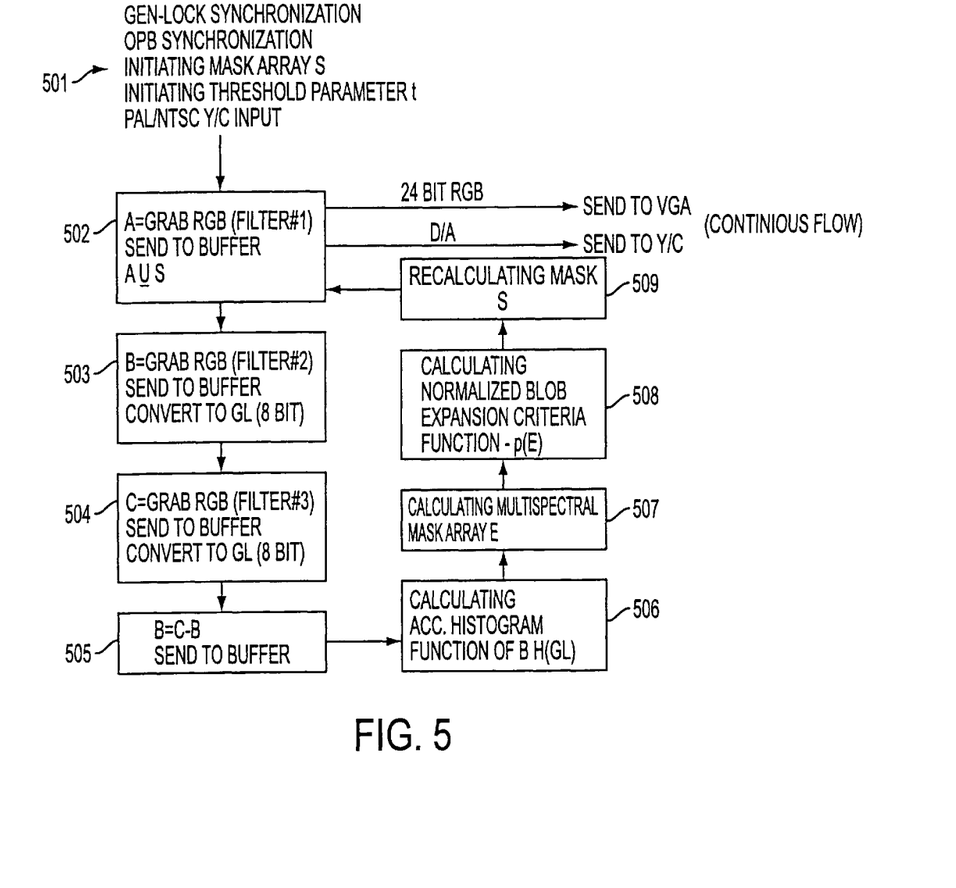
FIG. 5 illustrates a two band combined multi-spectral and spatial real time flow chart of mode b.

Algorithms description:

2 band combined multi-spectral & spatial real time algorithm (mode b)—FIG. 5

Step 501;

1) the system is set into run-mode (filter wheel starts moving)
2) TBC board starts synchronizing the camera frame rate (Gen-Lock) rectangular-wave with the filter wheel steps and the frame grabber buffer triggering
3) The Frame Grabber board indicates (using a minimum average method) when the OPB Blank-filter passed the "bridge" (CCD), giving a command for starting algorithm procedure from the next frame (i.e.— correspondingly with filter 1)

| | |
|---|---|
| 4) S = 0 | *Initiating a binary Mask array with zero values |
| 5) t = threshold | *Initiating multi-spectral threshold |
| Step 502; | |
| 6) A = Grab_Frame_RGB | *Grabbing color frame (filter 1) and assigned it as an 24 bit (RGB) array $A_{ij}$ |
| 7) Send_to_Buffer_1{A} | *Sending A-RGB array into a memory buffer 1 |
| $A = \begin{cases} R\{A\}US = R\{A\} \text{ if } S = 0, 255 \text{ if } S = 255 \\ G\{A\} \\ B\{A\} \end{cases}$ | |
| 9) Send_to_VGA {A} | *Outputting A-RGB array into VGA graphic card |
| 10) Send_to_Y/C{A} | *D/A transforming of A into an analog Y/C |
| Step 503; | |
| 11) B = Grab_Frame_RGB | *Grabbing color frame (filter 2) and assigned it as an 24bit (RGB) array $B_{ij}$ |
| 12) Send_to_Buffer_2{B} | *Sending B-RGB array into a memory buffer 2 |
| 13) TransformRGB_to_GL{B} | *Transforming 24bit RGB B array into an 8bit Gray level array via the transformation: $$RGB \rightarrow GL = \frac{R+G+B}{3}$$ |

-continued

| | |
|---|---|
| 14) Send_to_VGA{A} | *Outputting A-RGB array into VGA graphic card (updating VGA signal) |
| 15) Send_to_Y/C{A} | *D/A transforming of A into an analog Y/C (updating video signal} |

Step 504;

| | |
|---|---|
| 16) C = Grab_Frame_RGB | *Grabbing color frame (filter 3) and assigned it as an 24bit (RGB array $C_{ij}$ |
| 17) Send_to_Buffer_2{C} | *Sending B-RGB array into a memory buffer 3 |
| 18) TransformRGB_to_GL{C} | *Transforming 24bit RGB B array into an 8 bit Gray level array |
| 19) Send_to_VGA{A} | *Outputting A-RGB array into VGA graphic card (updating video signal) |

Step 505;

| | |
|---|---|
| 20) B = C − B | *D/A transforming of A into an analog Y/C (updating video signal} |
| 21) B = C − B | *updating buffer 2 with a new 8 bit (gray level) array which is the difference between array C and array B |
| 22) Send_to_VGA{A} | *Outputting A-RGB array into VGA graphic card (updating VGA signal while filter wheel is set on blank filter #4) |
| 23) Send_to_Y/C{A} | *D/A transforming of A into an analog Y/C (updating video signal while filter wheel is set on blank filter #4} |

Step 506;

| | |
|---|---|
| 24) H(GL) = Hist_Acc{B} | *Calculating the accumulated histogram Function of B(see below for histogram | discussion)

25) $$E = \begin{cases} 0 \text{ if } H < t \\ 255 \text{ if } H > t \end{cases}$$

*Multi-spectral Binary Mask Overlay Luck Up table, where t is a pre-defined threshold parameter (0 < t < 1) (stored in buffer #4)

Step 507;

26) S = blob{E}
*Updating Mask Array-S (Spatial Re-Masking of the Multi-spectral binary mask-E), by using a blob analysis applied on the 1st order Mask-E, where p is the normalized blob-expansion binary criteria function:

Step 508;

$$P(E) = \begin{cases} 0 \text{ if } E \notin \text{blob} \\ 1 \text{ if } E \in \text{blob} \end{cases}$$

$$S = \begin{cases} 0 \text{ if } p = 0 \\ 255 \text{ if } p = 1 \end{cases}$$

Step 509;

27) Re-continuing from step 6

Accumulated Histogram (Threshold Function, Adaptive Threshold Function)

This method has been developed in order to perform a "smart threshold" level, without being dependent on the temporal variations and extent over the dynamic range of the image histogram (means—# of pixels versus gray level value). This method is commonly used for masking, luck-up-table (LUT) conversion or other image-processing assisted algorithms.

Define a Raster histogram function:

$$n(GL)$$

where n is a number of pixels and GL is a gray level value within the system dynamic range (i.e. −0, 1,2,3. . . , 255 for 8 bit digitization).

Now, the Normalized Density Histogram Function is defined as:

$$P(GL) = \frac{n(GL)}{N} \quad (N = \text{total number of pixels})$$

Figure 7A:
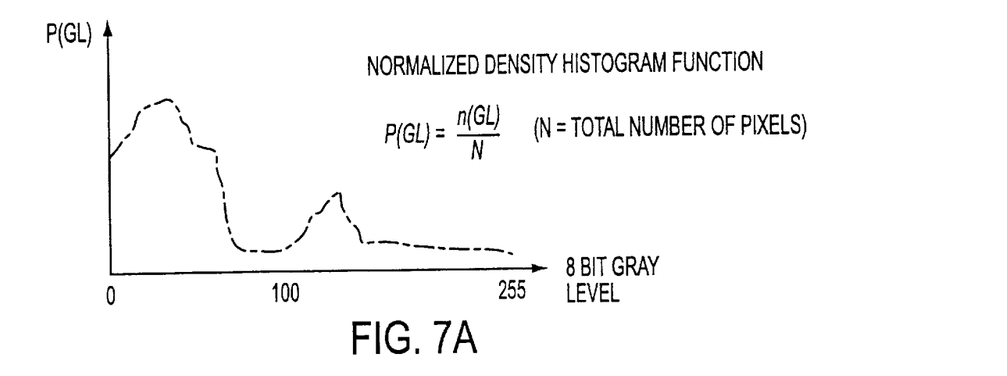
FIGS. 7a and 7b illustrate normalized density and accumulated histogram functions respectively.
Figure 7B:
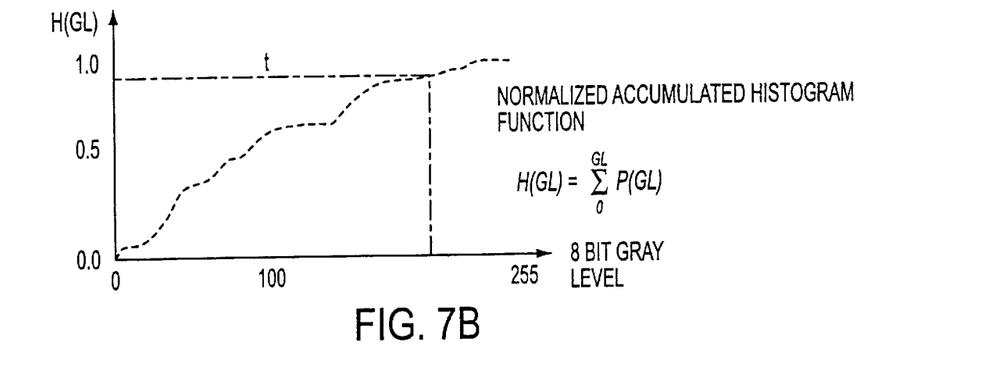

An example to P(GL) is illustrated in FIG. 7a. Normalization condition yields $$\sum_{0}^{255} P(GL) = 1$$

Normalized Accumulated Histogram Function is defined as:

$$H(GL) = \sum_{0}^{GL} P(GL)$$

H(GL) represents the fraction of pixels, accumulated from zero gray-level value up to a certain gray-level value level, with respect to the total number of pixels N. The meaning of that is: H(255)=1.0 and H(GL) is a continuously—increasing function with positive values:

$$0 \geq H(GL) \leq 1$$

Thus, the threshold parameter—t defines a criteria that differs between:

One. Gray-level values that are below accumulation (i.e.—0–GL', where GL' is calculated)

Two. The rest of gray levels extend from GL' to 255.

This action enable to create negative (considering range a) or positive (considering range b) mask arrays and/or LUT's (for instance—a positive LUT transforms into a zero value all the pixels with GL<GL' and keeps the former value of all the other pixels):

For instance—a "strong" threshold criteria is t=0.9 while a "weak" threshold criteria is t=0.5.

In simple words, by using this method the gray-level threshold (GL') is taken and extrapolated from a parameter t that present "most common" population or accumulation. Thus, for instance, for one raster most of the population is below GL'=50 while for the next one GL'=165.

From the physical aspect—this method is chosen in order to optimally compensate conditions of non-constant or unstable irradiation.

CONCLUSION

A system and method has been shown in the above embodiments for the effective implementation of a method and apparatus for differentiating and processing images of normal, benign and lesioned tissues using mixed reflected and autofluoresced light. While various preferred embodiments have been shown and described, it will be understood that there is no intent to limit the invention by such disclosure, but rather, it is intended to cover all modifications and alternate constructions falling within the spirit and scope of the invention as defined in the appended claims. For example, the present invention should not be limited by size, materials, connection methods, optical attachments (e.g. endoscopes, colposcopes, cystoscopes, etc.), processing methods or specified target tissues. The device may be used in the fields of gastroenterology, bronchoscopy or other similar medical procedures and includes applications to a wide range of other pre-malignancies, dysplastic lesions and superficial tumors. In addition, the optical photo bridge and/or optical encoders located within the stepping motor can optionally be used for a fine spatial recognition of the filter wheel status (instead of the blank filter start period trigger, monitored by the frame grabber software). This modification enables a replacement of the blank filter with an additional photopics (color) filter and, thus, doubling the system output presentation rate.

What is claimed is:

1. A method of detecting and displaying diseased tissue in real time comprising:
    a. illuminating a target tissue with a multi-spectral light source;
    b. establishing a starting point by an electronic capture of a dark field filter of a multi-sectional rotating filter wheel;
    c. rotating said multi-sectional rotating filter wheel to select a color filter;
    d. establishing a color image by an electronic capture of an imaged target tissue through said color filter;
    e. rotating said multi-sectional rotating filter wheel to select a maximum contrast filter;
    f. establishing a maximum contrast image by an electronic capture of an imaged target tissue through said maximum contrast filter;
    g. rotating said multi-sectional rotating filter wheel to select a minimum contrast filter;
    h. establishing a minimum contrast image by an electronic capture of an imaged target tissue through said minimum contrast filter;
    i. subtracting said minimum contrast data array from said maximum contrast data array;
    j. raster scanning, digitizing and storing in computer memory each of said captured images, and
    k. repeating steps a–j in synchronism to create an accumulated histogram;
    l. processing said accumulated histogram to ascertain the presence of binary large objects representing diseased tissue sections, and
    displaying said diseased tissue sections as an overlay on said color image.

2. A method of detecting and displaying diseased tissue in real time as per claim 1, wherein step a includes illuminating said target tissue with a metal halide light source.

3. A method of detecting and displaying diseased tissue in real time as per claim 2, wherein said metal halide source produces double excitation bands in the purple 420–470 nm and green 520–580 nm wavelengths.

4. A method of detecting and displaying diseased tissue in real time as per claim 2, wherein said metal halide light source produces both reflected and autofluorescence light which is retained during said maximum and minimum electronic capture steps.

5. A method of detecting and displaying diseased tissue in real time as per claim 1, wherein said electronic capture is performed by a camera.

6. A method of detecting and displaying diseased tissue in real time as per claim 5, wherein said camera further comprises a remote camera head.

7. A method of detecting and displaying diseased tissue in real time as per claim 6, wherein said remote camera head retains said multi-sectional rotating filter wheel.

8. A method of detecting and displaying diseased tissue in real time as per claim 7, wherein said remote camera head additionally retains a CCD image chip, stepper motor to rotate said multi-sectional rotating filter and optical elements.

9. A method of detecting and displaying diseased tissue in real time as per claim 1, wherein said target tissue is selected during an internal cervical or bladder inspection.

10. A multi-mode diagnostic method for differentiating normal and benign from pre-cancerous and cancerous lesioned tissue, said mode being one selected from a set consisting of tissue image inspection only, tissue image inspection and tissue image differentiation, and tissue image differentiation only, said method comprising the steps of:
   a) illuminating a target tissue with a predetermined spectrally mixed light from a source with double excitation bands in the blue-purple 420–470 nm region and the green 520–580 nm region, the excitation bands stimulating said target tissue fluorescence; and
   b) iteratively
      1) electronically capturing any reflected and autofluorescenced light returns from the target tissues with at least one raster scanned and filtered image of the returns selected as a function of the mode of use,
      2) iteratively processing the filtered returns from the (i) deriving a color light target tissue image from a photopic filter, (ii) deriving an image of high contrast among normal and benign and pre-cancerous and cancerous lesioned tissues from a maximal image contrast filter utilizing tissue reflected and autofluorescenced light, and (iii) identifying preselected types of artifacts utilizing the output of a minimal contrast filter and subtracting said identified artifacts from the output of the maximal contrast filter, and
      3) forming and communicating one or more images of the processed returns.

11. A multi-mode diagnostic method for differentiating normal and benign from pre-cancerous and cancerous lesioned tissue as per claim 10, wherein said predetermined spectrally mixed light comprises a metal halide light source.

12. A multi-mode diagnostic method for differentiating normal and benign from pre-cancerous and cancerous lesioned tissue as per claim 10, wherein said electronic capture step utilizes a camera and remote camera head.

13. A multi-mode diagnostic method for differentiating normal and benign from pre-cancerous and cancerous lesioned tissue as per claim 10, wherein said remote camera head retains a multi-sectional rotating filter wheel.

14. A multi-mode diagnostic method for differentiating normal and benign from pre-cancerous and cancerous lesioned tissue as per claim 13, wherein said remote camera head additionally retains a CCD image chip, stepper motor to rotate said multi-sectional rotating filter and optical elements.

15. A multi-mode diagnostic method for differentiating normal and benign from pre-cancerous and cancerous lesioned tissue as per claim 10, wherein said target tissue is located during an internal cervical or bladder inspection.

16. A multi-mode diagnostic method for differentiating normal and benign from pre-cancerous and cancerous lesioned tissue as per claim 10, wherein said step of electronically capturing any reflected and autofluorescenced light returns includes the step of cyclically obtaining a color image, and a maximal contrast image of the benign and lesioned tissues in the range of 500 nm.

17. A method for differentiating normal and benign from pre-cancerous and cancerous lesioned tissue comprising the steps of:
   a) illuminating target tissues with a preselected spectrally mixed light source as generated by a metal halide source in two excitation bands (blue-purple 420–470 nm and green 520–580 nm); and
   b) detecting and iteratively processing and electronically projecting the light echoes by:
      1) raster scanning and filtering the reflected and autofluorescenced light echoes to maximal contrast the echo returns from counterpart tissue regions and baseline compare with minimally differentiated echo returns from the same counterpart regions; and
      2) mapping raster scanned and filter processed returns into a video image of counterpart tissue regions of spectrally associated video effects of a first and second kind.

18. A method for differentiating normal and benign from pre-cancerous and cancerous lesioned tissue as per claim 17, wherein step (b)(1) of raster scanning and filtering includes the substep of filtering the echoes through a filter arrangement of an:
   (1) an IR cut-off filter for minimally distorted image,
   (2) an integrating filter responsive to light reflectance and autofluorescence for distinguishing benign and lesioned tissue (filter for maximum contrast),
   (3) a filter providing minimal contrast (reference filter), and
   (4) dark (no transmittance) filter to bridge to a next iteration.

19. A multi-mode diagnostic system for differentiating normal and benign from pre-cancerous and cancerous lesioned tissue, said mode being one selected from a set consisting of tissue image inspection only, tissue image inspection and tissue image differentiation, and tissue image differentiation only, said system comprising:
   a computer processing section;
   an ultra-bright metal halide light source;
   a digital processing camera connected to said computer processing section;
   a remote camera head comprising a CCD image chip, multiple filters, a filter selector, and optical elements;
   a real time frame grabber to capture raster images from said digital processing camera;
   a time base corrector to synchronize the selection of said filters to a scan rate of said digital processing camera, and
   wherein said ultra-bright metal halide light source is directed to a target tissue, reflected and autofluoresced light echoed from said target tissue is filtered, collected by the CCD of said remote camera head, captured by said digital processing camera, communicated to said frame grabber, processed to differentiate said normal and benign from pre-cancerous and cancerous lesioned tissues and displayed on an associated display in real time.

20. A method of detecting and displaying any of normal, benign, pre-cancerous and cancerous lesioned tissue in real time comprising:
   a. illuminating a target tissue with a multi-spectral light source;
   b. establishing imaging synchronization;
   c. selecting a color filter;
   d. establishing a color image by an electronic capture of an imaged target tissue through said color filter;
   e. selecting a maximum contrast filter;

f. establishing a maximum contrast image by an electronic capture of an imaged target tissue through said maximum contrast filter;

g. selecting a minimum contrast filter;

h. establishing a minimum contrast image by an electronic capture of an imaged target tissue through said minimum contrast filter;

i. subtracting said minimum contrast image from said maximum contrast image;

j. raster scanning, digitizing and storing in computer memory each of said captured images, and k. repeating steps a–j in synchronism to create an accumulated histogram;

l. processing said accumulated histogram to ascertain the presence of diseased tissue sections and creating an image thereof, and displaying any of the images: color, maximal contrast or diseased overlayed on color.

21. A method of detecting and displaying any of normal, benign, pre-cancerous and cancerous lesioned tissue in real time as per claim 20, wherein step a includes illuminating said target tissue with a metal halide light source.

22. A method of detecting and displaying any of normal, benign, pre-cancerous and cancerous lesioned tissue in real time as per claim 21, wherein said metal halide source produces double excitation bands in the blue-purple 420–470 nm and green 520–580 nm wavelengths.

23. A method of detecting and displaying any of normal, benign, pre-cancerous and cancerous lesioned tissue in real time as per claim 21, wherein said metal halide light source produces both reflected and autofluorescence light which is retained during said maximum and minimum electronic capture steps.

* * * * *